United States Patent [19]

Fuchs et al.

[11] 3,959,331
[45] May 25, 1976

[54] ALLOPHANIMIDATE HERBICIDES

[75] Inventors: Julius J. Fuchs, Wilmington; Kang Lin, Newark, both of Del.

[73] Assignee: E. I. Du Pont de Nemours and Company, Wilmington, Del.

[22] Filed: Jan. 22, 1973

[21] Appl. No.: 325,357

Related U.S. Application Data

[63] Continuation-in-part of Ser. No. 181,201, Sept. 16, 1971, abandoned.

[52] U.S. Cl. ............................. 260/455 A; 71/98; 71/99; 71/100; 71/101; 71/106; 260/465 D; 260/465 E; 260/468 E; 260/470; 260/471 C; 260/479 C; 260/481 C; 260/482 C; 260/553 A; 260/553 R
[51] Int. Cl.² ............................. C07C 157/14
[58] Field of Search ............ 260/471 C, 455 A

[56] References Cited
UNITED STATES PATENTS 3,636,079   1/1972   Koenig et al..................... 260/471 C

*Primary Examiner*—James A. Patten

[57] ABSTRACT

Allophanimidates and carbamates of the formulas

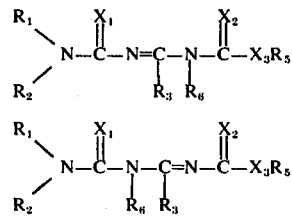

where
 R₁ is hydrogen or alkyl;
 R₂ is alkyl, cycloalkyl, cycloalkylalkyl, alkenyl, alkynyl, benzyl or phenyl optionally substituted;
 R₃ is SR₄ or OR₄;
 R₄ is alkyl, cycloalkyl, alkenyl, alkynyl, phenyl, or benzyl;
 R₅ is alkyl, alkenyl, cycloalkyl, benzyl or phenyl optionally substituted; and
 R₆ is hydrogen or alkyl
 X₁, X₂ and X₃ are oxygen or sulfur, are useful as herbicides.

Exemplary of the compounds is methyl 4-tert-butyl-N-methoxycarbonyl-1-thioallophanimidate.

3 Claims, No Drawings

ALLOPHANIMIDATE HERBICIDES

CROSS REFERENCE TO RELATED APPLICATION

This application is a continuation-in-part of application Ser. No. 181,201, filed Sept. 16, 1971, now abandoned.

BACKGROUND OF THE INVENTION

Organic Synthesis, 42, 87, discloses preparation of methyl 4-phenyl-3-thioallophanimidate, but does not disclose any use for the compound.

SUMMARY OF THE INVENTION

We have discovered that the compounds of the following formulas I and II are useful as herbicides, i.e., they are useful as soil sterilants and as selective herbicides on crops such as corn, asparagus, pineapple and sugarcane:

Formula I            Formula II

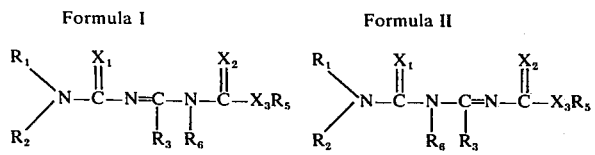

wherein
$X_1$, $X_2$, and $X_3$ are oxygen or sulfur;
$R_1$ is hydrogen or alkyl of 1 through 4 carbon atoms;
$R_2$ is alkyl of 1 through 6 carbon atoms, cycloalkyl of 3 through 8 carbon atoms, cycloalkylalkyl of 4 through 7 carbon atoms, alkenyl of 3 through 4 carbon atoms, alkynyl of 3 through 4 carbon atoms, benzyl, or

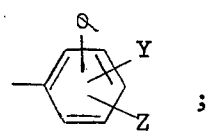

where
Y is hydrogen, halogen, alkyl of 1 through 4 carbon atoms, nitro, alkoxy of 1 through 4 carbon atoms, alkylthio of 1 through 4 carbon atoms, cyano, or trifluoromethyl; and
Z is hydrogen, halogen, methyl, ethyl, nitro, alkoxy of 1 through 4 carbon atoms, or alkylthio of 1 through 4 carbon atoms;
O is hydrogen, halogen, or methyl;
$R_3$ is $SR_4$ or $OR_4$;
where
$R_4$ is alkyl of 1 through 6 carbon atoms,
cycloalkyl of 3 through 8 carbon atoms,
alkenyl of 3 through 4 carbon atoms, alkynyl of 3 through 4 carbon atoms, benzyl or phenyl; and
$R_5$ is alkyl of 1 through 12 carbon atoms substituted with 0–3 chlorine atoms or 0–1 methoxy group, alkenyl of 3 through 4 carbon atoms, cycloalkyl of 5 through 8 carbon atoms, benzyl, or

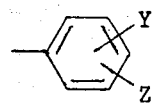

where
Y and Z are as previously defined;
$R_6$ is hydrogen or alkyl 1 through 3 carbon atoms.
Preferred within Formula I because of ease of synthesis and higher activity are those compounds where
$R_1$ is hydrogen;
$R_2$ is alkyl of 1 through 6 carbon atoms, alkenyl of 3 through 4 carbon atoms, or phenyl substituted with 0–3 halogens selected from chlorine and bromine;
$R_3$ is $SR_4$ or $OR_4$;
$R_4$ is alkyl of 1 throughh 6 carbon atoms or allyl;
$R_5$ is alkyl of 1 through 4 carbon atoms;
$R_6$ is hydrogen or methyl;
$X_1$ and $X_2$ are oxygen; and
$X_3$ is oxygen or sulfur.
More preferred because of their highest activity are those compounds where
$R_1$ is hydrogen;
$R_2$ is alkyl of 3 through 4 carbon atoms;
$R_3$ is $SR_4$ or $OR_4$;
$R_4$ is methyl or ethyl;
$R_5$ is methyl or ethyl;
$R_6$ is hydrogen;
$X_1$ and $X_2$ are oxygen; and
$X_3$ is oxygen or sulfur.
Preferred compounds because of their high activity are:
methyl 4-tert-butyl-N-methoxycarbonyl-1-thioallophanimidate
methyl 4-tert-butyl-N-methylthiolcarbonyl-1-thioallophanimidate
methyl 4-isopropyl-N-methoxycarbonyl-1-thioallophanimidate
methyl 4-isopropyl-N-ethoxycarbonyl-1-thioallophanimidate
methyl 4-isopropyl-N-isopropoxycarbonyl-1-thioallophanimidate
It should be understood that tautomeric forms of the molecule are possible when $R_6$ is hydrogen;

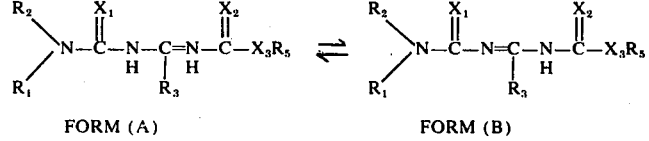

FORM (A)            FORM (B)

For this reason, all compounds when $R_6$ is hydrogen are named allophanimidates according to form (A). Compounds of Form (C) are also named as allophanimidates, while compounds of Form (D) are named as carbamates.

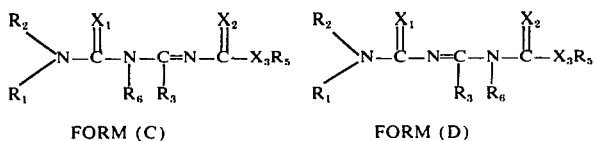

FORM (C)    FORM (D)

DETAILED DESCRIPTION OF THE INVENTION

The compounds of the invention can be made by the process illustrated by the following equations:

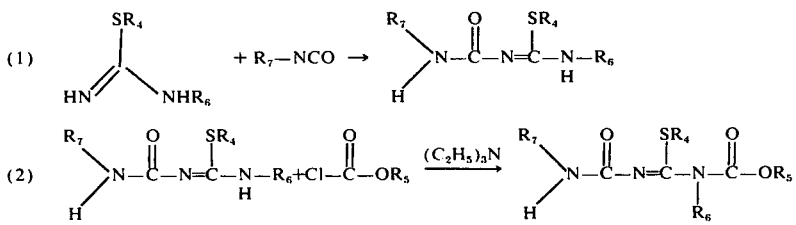

where
R$_4$, R$_5$ and R$_6$ are as previously defined and
R$_7$ is R$_1$ or R$_2$.

In equation (1) the 2-thiopseudourea is liberated from its corresponding chloride or sulfate with one mole of base and reacted with an isocyanate in a solvent, e.g., water, aqueous methanol or aqueous acetone, at about 0°C. The reaction mass is warmed to room temperature and the solvent removed by evaporation. The intermediate thioallophanimidate is collected by filtration and dried (This reaction is essentially the same method as described in Organic Synthesis, 42, 87, for the preparation of methyl 4-phenyl-3-thioallophanimidate).

The intermediate is reacted with one equivalent of a chloroformate in methylene chloride containing one equivalent of triethylamine (equation 2). The methylene chloride solution is washed with water, dried, and stripped to afford the thioallophanimidates of this invention in good purity. The reaction product can be further purified by dissolving it in dimethylformamide and precipitating it by adding water or by recrystallization from hexane.

The same allophanimidates can also be obtained by reacting the 2-thiopseudourea first with a chloroformate and then an isocyanate as in equations 3 and 4.

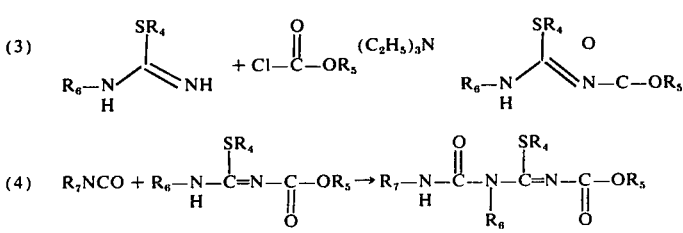

where R$_4$, R$_5$, R$_6$ and R$_7$ are as defined for equations (1) and (2).

In Equation (3) the 2-thiopseudourea sulfate and a chloroformate in water are cooled to about 0°C. and two equivalents of base are added gradually. The reaction mixture is allowed to come to room temperature and then extracted with methylene chloride. The methylene extract is dried and evaporated to afford the intermediate alkyl N-(1-alkylamino-1-methylthiomethylene)carbamate or alkyl-(1-amino-1-methylthiomethylene)carbamate in excellent purity.

In equation (4) the intermediate is dissolved in methylene chloride and one equivalent of isocyanate is added. The mixture is stirred for several hours, and then evaporated to produce the allophanimidates in excellent yield and purity. The product can be further purified using the techniques set forth above.

To make the various analogs of the above compounds, the appropriate isothiocyanates can replace the isocyanates used in the equations (1) and (4). The useful 2-thiopseudoureas of equations (1) and (3) can be replaced by 2-alkylpseudoureas. The useful chloroformates of equations (2) and (4) include alkyl chloroformates, chlorothiolformates, or chlorodithioformates.

Alkoxycarbonylthioallophanimidates with 2 alkyl substituents in the 4-position can be prepared by starting with the product of reaction (3) and reacting it with a dialkylcarbamoyl chloride in the presence of triethylamine as illustrated by reaction (5).

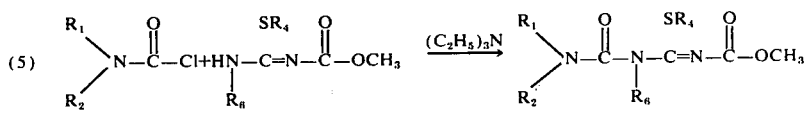

In reaction (5) the reactants are heated for 1–3 hours in the presence of triethylamine in a solvent such as benzene or toluene. After completion of the reaction, the solvent is evaporated, the residue extracted with water to dissolve water-soluble substances, and the residue recrystallized from benzene.

The following examples are offered to illustrate the processes described above. All parts are parts by weight unless otherwise indicated.

EXAMPLE 1

Methyl 4-tert-butyl-N-methylthiolcarbonyl-1-thioallophanimidate

To 139 parts 2-methyl-2-thiopsuedourea sulfate in 1000 parts 50% aqueous methanol at 0°C. is added dropwise 88 parts 50% sodium hydroxide, followed by 90 parts tert-butylisocyanate in 200 parts tetrahydrofuran. The solution is then stripped of most of the methanol and tetrahydrofuran on a rotary evaporator and filtered to yield after drying 90 parts methyl 4-tert-butyl-1-thioallophanimidate melting at 102°–104°C.

To 5.67 parts of the above compound and 4 parts triethylamine in 50 parts methylene chloride at 0°C. is added dropwise 3.3 parts methyl chlorothiolformate in 5 parts methylene chloride. The solution is stirred overnight and washed once with water. After drying and evaporation of the solvent on a rotary evaporator, there is obtained 3.8 parts methyl 4-tert-butyl-N-methylthiolcarbonyl-1-thioallophanimidate melting at 102°–105°C.

EXAMPLE 2

4-tert-Butyl-N-methoxycarbonyl-1-thioallophanimidate

To 5.67 parts of methyl 4-tert-butyl-1-thioallophanimidate, prepared as in Example 1, and 4 parts of triethylamine in 50 parts methylene chloride at 0°C. is added dropwise 2.8 parts methyl chloroformate in 5 parts methylene chloride. The solution is stirred overnight and washed once with water. After drying and evaporation of the solvent on a rotary evaporator, there is obtained an oil which turned crystalline. After trituration with hexane it affords 1.9 parts 4-tert-butyl-N-methoxycarbonyl-1-thioallophanimidate melting at 87°–90°C.

EXAMPLE 3

Methyl 4-isopropyl-N-methoxycarbonyl-1-thioallophanimidate

To 69.5 parts 2-methyl-2-thiopseudourea sulfate and 47 parts of methyl chloroformate in 1,000 parts water at 0°C is added dropwise 56.9 parts of potassium hydroxide in 200 parts of water. The reaction mixture is stirred at room temperature for 3 hours and then extracted with methylene chloride. The methylene chloride extract is dried and the solvent evaporated on a rotary evaporator to give 45 parts of methyl N-(1-amino-1-methylthiomethylene)carbamate melting at 72°–77°C.

Seventy-four parts of the above compound and 47 parts of isopropyl isocyanate in 300 parts methylene chloride is stirred overnight. The solvent is evaporated on a rotary evaporator to give 113.6 parts methyl 4-isopropyl-N-methoxycarbonyl-1-thioallophanimidate melting at 129°–132°C.

The following allophanimidates can be similarly prepared: methyl 4-cyclopentyl-2-methyl-N-methoxycarbonyl-1-thioallophanimiate, and methyl 4-cyclohexyl-2-propyl-N-methoxycarbonyl-1-thioallophanimidate.

EXAMPLE 4

Methyl 4-methyl-N-methylthiolcarbonyl-1-thioallophanimidate

To 69.5 parts 2-methyl-2-thiopseudourea sulfate and 110 parts methyl chlorothioformate in 500 ml. of water is added dropwise at 0°–5°C. 120 parts 50% sodium hydroxide. The reaction mixture is stirred at 0°–5°C. for 1 hour and then at room temperature for 2 hours. The solution is extracted with methylene chloride. The methylene chloride extract is then dried and the solvent evaporated on a rotary evaporator to give 47 parts of methyl N-(1-amino-1-methylthiomethylene)thiocarbamate melting at 75°–76°C.

To 8.2 parts of the above compound in 75 parts methylene chloride is added 3.1 parts methyl isocyanate. The reaction mixture is stirred at room temperature for 3 hours, and then stripped of solvent on a rotary evaporator to give 10 parts methyl 4-methyl-N-methylthiocarbonyl-1-thioallophanimidate melting at 115°–117°C.

EXAMPLE 5

Methyl 4-(p-chlorophenyl)-N-methoxycarbonyl-1-thioallophanimidate

To 7.2 parts methyl N-(1-amino-1-methylthiomethylene)carbamate prepared as in Example 3 in 100 parts methylene chloride is added 8.4 parts p-chlorophenyl isocyanate. The reaction mixture is stirred overnight and the solvent evaporated on a rotary evaporator. The residue is dissolved in dimethylformamide and water is added. The precipitate is collected by filtration and then dried to give 10.4 parts methyl 4-chlorophenyl)-N-methoxycarbonyl-1-thioallophanimidate melting at 73°–74.5°C.

EXAMPLE 6

Methyl 4-sec-butyl-N-methoxycarbonyl-1-thioallophanimidate

To 7.2 parts methyl N-(1-amino-1-methylthiomethylene)carbamate, prepared as in Example 3, in 50 parts methylene chloride is added 5.5 parts sec-butylisocyanate. The reaction mixture is stirred overnight and the solvent is evaporated on a rotary evaporator to give 12 parts methyl 4-sec-butyl-N-methoxycarbonyl-1-thioallophanimidate melting at 102°–104°C.

EXAMPLE 7

Methyl 4-isopropyl-N-ethoxycarbonyl-1-thioallophanimidate

To 138 parts 2-methyl-2-thiopseudourea in 500 parts water at 0°–10°C. is added 80 parts 50% sodium hydroxide. One liter of cold acetone is added followed by dropwise addition of 85 parts isopropyl isocyanate. The mixture is allowed to stay at room temperature for 2 hours and evaporated on a rotary evaporator. The solid is collected and dried to give 150 parts methyl 4-isopropyl-1-thioallophanimidate melting at 81°–85°C.

To 8.8 parts of the above compound and 6.0 parts ethyl chloroformate at 0°C. is added dropwise 8.4 parts triethylamine. The reaction is stirred at room temperature for 3 hours. Water is added and stirred for a while. The methylene chloride layer is dried and evaporated on a rotary evaporator to give after hexane trituration, 10.2 parts methyl 4-isopropyl-N-ethoxycarbonyl-1-thioallophanimidate melting at 90°–92°C.

EXAMPLE 8

Methyl 4-propyl-N-methoxycarbonyl-1-thioallophanimidate

To 7.4 parts of methyl N-(1-amino-1-methylthiomethylene)carbamate prepared as in Example 3 in 50 parts of methylene chloride is added 4.7 parts of propyl isocyanate. The reaction mixture is stirred overnight and the solvent is stripped on a rotary evaporator to give a solid which is dissolved in benzene and precipitated by adding hexane. The solid is collected and dried to give 10 parts of methyl 4-propyl-N-methoxycarbonyl-1-thioallophanimidate melting at 68°–69°C.

EXAMPLE 9

Methyl 4-(p-chlorophenyl)-N-methoxycarbonyl allophanimidate

To 13 parts of methyl N-(1-amino-1-methoxymethylene)carbamate, m.p. 36°–39.5°, prepared similar to the procedure in Example 3 for methyl N-(1-amino-1-methylthiomethylene)carbamate in 140 parts of methylene chloride is added 15 parts of p-chlorophenyl isocyanate. The reaction mixture is stirred overnight and the solution filtered to give 10 parts of methyl 4-(p-chlorophenyl)-N-methoxycarbonylallophanimidate melting at 170° dec.

EXAMPLE 10

Methyl 4-(p-chlorophenyl)-N-methylthiolcarbonylallophanimidate

To 9 parts by weight N-(1-amino-1-methoxymethylene)thiocarbamate, m.p. 55°–57°, prepared similar to the procedure in Example 3 for methyl N-(1-amino-1-methylthiomethylene)carbamate in 20 parts of methylene chloride is added 9 parts of p-chlorophenyl isocyanate. The reaction mixture is stirred overnight and the solution is filtered to give 14 parts of methyl 4-(p-chlorophenyl)-N-methylthiolcarbonylallophanimidate melting at 153°–155°.

The following allophanimidates can be prepared by the procedure of Example 2 by substituting the listed 2-substituted thiopseudoureas and pseudoureas for 2-methyl-2-thiopseudourea, by replacing tert-butylisocyanate with various isocyanates or isothiocyanates, and by using various chloroformates, chlorothiolformates, or chlorodithioformates in place of methyl chloroformate.

| Pseudothiourea or Psueodurea | Isocyanate or Isothiocyanate | Formate, Thiolformate or Dithioformate | Allophanimidates |
| --- | --- | --- | --- |
| 2-hexyl-2-thiopseudourea | methyl isocyanate | methyl chloroformate | hexyl 4-methyl-N-methoxycarbonyl-1-thioallophanimidate |
| 2-methyl-2-thiopseudourea | hexyl isocyanate | phenyl chloroformate | methyl 4-hexyl-N-phenoxycarbonyl-1-thioallophanimidate |
| 2-cyclopropyl-2-thiopseudourea | cyclopropyl isocyanate | p-chlorophenyl chloroformate | cyclopropyl 4-cyclopropyl-N-(p-chlorophenoxycarbonyl)-1-thioallophanimidate |
| 2-cyclooctyl-2-thiopseudourea | cyclooctyl isocyanate | m-bromophenyl chloroformate | cyclooctyl 4-cyclooctyl-N-(m-bromophenoxycarbonyl)-1-thioallophanimidate |
| 2-allyl-2-thiopseudourea | cyclohexylmethyl isocyanate | o-iodophenyl chloroformate | allyl 4-cyclohexylmethyl-N-(o-iodophenoxycarbonyl)-1-thioallophanimidate |
| 2-(3-methylallyl)-2-thiopseudourea | allyl isocyanate | o-fluorophenyl chloroformate | 3-methylallyl 4-allyl-N-(o-fluorophenoxycarbonyl)-1-thioallophanimidate |
| 2-methylpseudourea | 3-methylallyl isocyanate | p-methylphenyl chloroformate | methyl 4-(3-methylallyl)-N-(p-methylphenoxycarbonyl)-allophanimidate |
| 2-hexyl-2-thiopseudourea | propargyl isocyanate | m-ethylphenyl chloroformate | hexyl 4-propargyl-N-(m-ethylphenoxycarbonyl)-1-thioallophanimidate |
| 2-(3-methylpropargyl)-2-thiopseudourea | cyclopropylmethyl isocyanate | methyl chloroformate | 3-methylpropargyl 4-cyclopropylmethyl-N-methoxycarbonyl-1-thioallophanimidate |
| 2-cyclopropylpseudourea | 3-methylpropargyl isocyanate | p-nitrophenyl chloroformate | cyclopropyl 4-(3-methylpropargyl)-N-(p-nitrophenoxycarbonyl)-allophanimidate |
| 2-cyclooctylpseudourea | benzyl isocyanate | p-methoxyphenyl chloroformate | cyclooctyl 4-benzyl-N-(p-methoxyphenoxycarbonyl)-allophanimidate |
| 2-allylpseudourea | phenyl isocyanate | dodecyl chloroformate | allyl 4-phenyl-N-dodecyloxycarbonyl-allophanimidate |
| 2-(3-methylallyl)pseudourea | p-chlorophenyl isocyanate | allyl chloroformate | 3-methylallyl 4-(p-chlorophenyl)-N-allyloxycarbonyl-allophanimidate |
| 2-methyl-2-thiopseudourea | m-bromophenyl isocyanate | 3-methylallyl chloroformate | methyl 4-(m-bromophenyl)-N-(3-methylallyloxycarbonyl)-1-thioallophanimidate |
| 2-methyl-2-thiopseudourea | o-iodophenyl isocyanate | cyclopentyl chloroformate | methyl 4-(o-iodophenyl)-N-(cyclopentyloxycarbonyl)-1-thioallophanimidate |
| 2-methyl-2-thiopseudourea | o-fluorophenyl isocyanate | cyclooctyl chloroformate | methyl 4-(o-fluorophenyl)-N-cyclooctyloxycarbonyl-1-thioallophanimidate |
| 2-methyl-2-thiopseudourea | p-methylphenyl isocyanate | benzyl chloroformate | methyl 4-(p-methylphenyl)-N-benzyloxycarbonyl-1-thioallophanimidate |
| 2-methyl-2-thiopseudourea | m-ethylphenyl isocyanate | methyl chlorothiolformate | methyl 4-(m-ethylphenyl)-N-methylthiolcarbonyl-1-thioallophanimidate |
| 2-methyl-2-thiopseudourea | p-nitrophenyl isocyanate | m-butoxyphenyl chlorothiolformate | methyl 4-(p-nitrophenyl)-N-(m-butoxyphenylthiolcarbonyl)-1-thioallophanimidate |

-continued

| Pseudothiourea or Psueodurea | Isocyanate or Isothiocyanate | Formate, Thiolformate or Dithioformate | Allophanimidates |
|---|---|---|---|
| 2-methyl-2-thiopseudourea | p-methoxyphenyl isothiocyanate | p-methylthiophenyl chlorothiolformate | methyl 4-(p-methoxyphenyl)-N-(p-methyl-thiophenylthiocarbonyl)-1,3-dithio-allophanimidate |
| 2-methyl-2-thiopseudourea | m-butyloxyphenyl isothiocyanate | m-butylthiophenyl chlorothiolformate | methyl 4-(m-butoxyphenyl)-N-(m-butyl-thiophenylthiolcarbonyl)-1,3-dithio-allophanimidate |
| 2-methyl-2-thiopseudourea | p-methylthiophenyl isothiocyanate | m-trifluoromethyl-phenyl chloro-thiolformate | methyl 4-(p-methylthiophenyl)-N-(m-trifluoromethylphenylthiolcarbonyl)-1,3-dithioallophanimidate |
| 2-methyl-2-thiopseudourea | m-butylthiophenyl isothiocyanate | p-cyanophenyl chlorothiolformate | methyl 4-(m-butylthiophenyl)-N-(p-cyano-phenylthiolcarbonyl)-1,3-dithio-allophanimidate |
| 2-methyl-2-thiopseudourea | m-trifluoromethyl-phenyl isothiocyanate | 3,4-dichlorophenyl chlorothiolformate | methyl 4-(m-trifluoromethylphenyl)-N-3,4-dichlorophenylthiolcarbonyl)-1,3-dithioallophanimidate |
| 2-methyl-2-thiopseudourea | p-cyanophenyl isothiocyanate | methyl dithio-formate | methyl 4-(p-cyanophenyl)-N-(methylthiol-thiocarbonyl)-1,3-dithioallophanimidate |
| 2-phenyl-2-thiopseudourea | 3,4-dichlorophenyl isothiocyanate | 3,5-dichlorophenyl chlorodithiofor-mate | phenyl 4-(3,4-dichlorophenyl)-N-(3,5-dichlorophenylthiolthiocarbonyl)-1,3-dithioallophanimidate |
| 2-benzyl-2-thiopseudourea | 3,5-dichlorophenyl isothiocyanate | o-chloro-p-methyl-phenyl chlorodi-thioformate | benzyl 4-(3,5-dichlorophenyl)-N-(o-chloro-p-methylphenylthiolthiocar-bonyl)-1,3-dithioallophanimidate |
| 2-propargyl-2-thio-pseudourea | o-chloro-p-methyl-phenyl isothio-cyanate | 2,4-dinitrophenyl chlorodithiofor-mate | propargyl 4-(o-chloro-p-methylphenyl)-N-(2,4-dinitrophenylthiolthiocarbonyl)-1,3-dithioallophanimidate |
| 2-methylpseudourea | p-chlorophenyl iso-cyanate | chloroformate methoxyethyl | methyl 4-(p-chlorophenyl)-N-(2-methoxy-ethoxycarbonyl)allophanimidate |
| 2-methylpseudourea | p-chlorophenyl iso-cyanate | 2,2,2-trichloroethyl chloroformate | methyl 4-(p-chlorophenyl)-N-(2,2,2-trichloroethoxycarbonyl)allophanimidate |
| 2-methylpseudourea | 2-bromo-4,6-dichloro-phenyl isocyanata | methyl chloroformate | methyl 4-(2-bromo-4,6-dichlorophenyl)-N-methoxycarbonylallophanimidate |
| 2-methylpseudourea | 2,4,5-trichloro-phenyl isocyanate | methyl chloroformate | methyl 4-(2,4,5-trichlorphenyl)-N-methoxycarbonylallophanimidate |
| 2-methylpseudourea | 2,4,6-trimethyl-phenyl isocyanate | methyl chloroformate | methyl 4-(2,4,6-trimethylphenyl)-N-methoxycarbonylallophanimidate |
| 2-methylpseudourea | 2,4-dichloro-6-methylphenyl isocyanate | methyl chloroformate | methyl 4-(2,4-dichloro-6-methylphenyl)-N-methoxycarbonylallophanimidate |
| 2-methylpseudourea | p-bromophenyl iso-cyanate | methyl chloroformate | methyl 4-(p-bromophenyl)-N-methoxy-carbonylallophanimidate |
| 2-methylpseudourea | p-bromophenyl iso-cyanate | methyl chlorothiol-formate | methyl 4-(p-bromophenyl)-N-methylthiol-carbonylallophanimidate |
| 2-methylpseudourea | p-methylphenyl iso-cyanate | methyl chloroformate | methyl 4-(p-methylphenyl)-N-methoxy-carbonylallophanimidate |
| 2-methylpseudourea | p-methylphenyl iso-cyanate | methyl chlorothiol-formate | methyl 4-(p-methylphenyl)-N-methylthiol-carbonylallophanimidate |
| 2-methylpseudourea | p-methoxyphenyl iso-cyanate | methyl chloroformate | methyl 4-(p-methoxyphenyl)-N-methoxy-carbonylallophanimidate |
| 2-methylpseudourea | p-methoxyphenyl iso-cyanate | methyl chloroformate | methyl 4-(p-methoxyphenyl)-N-methylthiol-carbonylallophanimidate |
| 2-methylpseudourea | p-fluorophenyl iso-cyanate | methyl chloroformate | methyl 4-(p-fluorophenyl)-N-methoxy-carbonylallophanimidate |
| 2-methylpseudourea | p-fluorophenyl iso-cyanate | methyl chlorothiol-formate | methyl 4-(p-fluorophenyl)-N-methylthiol-carbonylallophanimidate |
| 2-methylpseudourea | 2,4-dichlorophenyl isocyanate | methyl chloroformate | methyl 4-(2,4-dichlorophenyl)-N-methoxy-carbonylallophanimidate |
| 2-methylpseudourea | 2,4-dichlorophenyl isocyanate | methyl chlorothiol-formate | methyl 4-(2,4-dichlorophenyl)-N-methyl-thiolcarbonylallophanimidate |
| 2-methylpseudourea | m-butylphenyl isocyanate | m-butylphenyl chloroformate | methyl 4-(m-butylphenyl)-N-(m-butyl-phenoxycarbonyl)-allophanimidate |

Similarly, the following carbamates can be prepared.

| Pseudothiourea, or Pseudourea | Isocyanate or Isothiocyanate | Formate, Thiolformate or Dithioformate | Carbamates |
|---|---|---|---|
| 1,2-dimethyl-2-thiopseudo-urea | cyclopentyl iso-cyanate | methyl chloroformate | methyl N-(1-cyclopentylcarbamylimino-1-methylthiomethyl)-N-methylcarbamate |
| 1,2-dimethyl-2-thiopseudo-urea | cyclohexyl iso-cyanate | methyl chloroformate | methyl N-(1-cyclohexylcarbamylimino-1-methylthiomethyl)-N-methylcarbamate |
| 2-methyl-1-propyl-2-thiopseudourea | cyclopentyl iso-cyanate | methyl chloroformate | methyl N-(1-cyclopentylcarbamylimino-1-methylthiomethyl)-N-propylcarbamate |
| 1,2-dimethyl pseudourea | p-chlorophenyl isocyanate | methyl chloroformate | methyl N-(1-p-chlorophenylcarbamyl-imino-1-methoxymethyl)-N-methyl-carbamate |

EXAMPLE 11

Methyl 4,4-dimethyl-N-methoxycarbonyl-1-thioallophanimidate

To a solution of 14.8 parts of N-(1-amino-1-methylthiomethylene)carbamate and 10.1 parts of triethylamine in 100 parts of benzene is added 11 parts dimethylcarbamoyl chloride and the reaction mixture refluxed for two hours. The reaction mixture is then subjected to vacuum and the solvent evaporated. The residue is then triturated with 200 parts of water at room temperature. The remaining solids are then recrystalized from benzene to give pure methyl 4,4-dimethyl-N-methoxycarbonyl-1-thioallophanimidate.

By using appropriate starting materials, the following compounds can be prepared in the same manner.

methyl 4,4-diethyl-N-methoxycarbonyl-thioallophanimidate methyl 4-methyl-4-butyl-N-methoxycarbonyl-1-thioallophanimidate The compounds of this invention are useful as herbicides. They may be used at rates of 5 to 40 kg/ha to control all vegetation in industrial sites, along rights-of-way, pipelines, tank farms, etc. At rates of 0.5 to 10 kg/ha certain of these compounds may be used for selective weed control in asparagus, pineapple, sugarcane, sisal, alfalfa, and corn. The precise rate of material to use in any situation will depend upon the weeds to be controlled, climatic and edaphic conditions and whether or not selective weed control is desired.

Among the weeds that can be controlled by the compounds of the invention are chickweed (*Stelaria media*), henbit (*Lamicum amplexicaule*), mustard (*Brassica spp.*), wild lettuce (*Lactuca spp.*), dandelion (*Taraxacun afficinale*), crabgrass (*Digitara spp.*), barnyardgrass (*Echinochloa crusgalli*), foxtail (*Setaria spp.*), fireweed (*Erechtites hieracifolia*), false vervain (*Stachytarpheta cayannensis*), richardia (*Richardia scabra*), pigweed (*Amaranthus retroflexus*), morningglory (*Ipomea spp.*), velvetleaf (*Abutilon theophrasti*), goosegrass (*Eleucine indica*), lambsquarters (*Chenopodium album*), teaweed (*Sida spinosa*), trumpetcreeper (*Campsis radicans*), Wild strawberry (*Fragaria viriniana*), broomsedge (*Andropogon virginicus*), bermudagrass (*Cynodon dactylon*), nutsedge (*Cyperus sp.*), and quackgrass (*Agropyron repens*).

The compounds of this invention may be combined with other herbicides such as bromacil, 3-sec-butyl-5-bromo-6-methyluracil; diuron, 3-(3,4-dichlorophenyl-1,1-dimethylurea; paraquet, 1,1'-dimethyl-4,4'-bipyridinium ion; 1,1-dimethyl-3,3-(N-tert-butylcarbamoyloxyphenyl)urea; 4-amino-6-tert-butyl-3-methylthio-as-triazine-5(4H)-one; and the s-triazines such as 2-chloro-4-ethylamino-6-isopropylamino-s-triazine to control a broader spectrum of weeds.

The compositions of the invention can be prepared by mixing at least one compound of either Formula (I) or (II) with a herbicidal adjuvant or modifier to provide compositions in the form of dusts, granules, pellets, water-dispersible powders, high-strength concentrates, aqueous dispersions or emulsions and solutions or dispersions in organic liquids.

Thus, the compounds of the invention can be used with herbicidal adjuvants, e.g., a carrier or diluent agent such as a finely divided solid, an organic liquid, water, a wetting agent, a dispersing agent, an emulsifying agent, or any suitable combination of these.

Compositions of the invention, especially liquids and wettable powders, contain as a conditioning agent one or more surface-active agents, sometimes called surfactants, in amounts sufficient to render a given composition containing the compounds of the invention readily dispersible in water or in oil.

The following paragraphs describe different types of herbicidal compositions of the compounds of the invention.

A. WETTABLE POWDERS

Wettable powders are water-dispersible compositions containing the active material, an inert solid extender, and one or more surfactants to provide rapid wetting and prevent heavy flocculation when suspended in water.

The inert extenders which are preferred for use in the wettable powders of this invention containing the compounds of the invention are of mineral origin.

The classes of extenders suitable for the wettable powder formulations of this invention are the natural clays, diatomaceous earth, and synthetic mineral fillers derived from silica and silicate. Most preferred fillers for this invention are kaolinites, attapulgite clay, montmorillonite clays, synthetic silicas, synthetic magnesium silicate and calcium sulfate dihydrate.

Suitable surfactants for use in such compositions are those listed by J. W. McCutcheon in "Detergents and Emulsifiers" 1970 Annual. Among the most preferred surfactants are the nonionic and anionic type, and those most suitable for the preparation of the dry, wettable products of this invention are solid forms of compounds known to the art as wetters and dispersants. Occasionally a liquid, nonionic compound classified primarily as an emulsifier may serve as both wetter and dispersant.

Most preferred wetting agents are alkylbenzene and alkylnaphthalene sulfonates, sulfated fatty alcohols, amines or acid amides, long chain acid esters of sodium isethionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

Wetting and dispersing agent in these preferred wettable powder compositions of this invention are usually present at concentrations of from about 0.5 weight percent to 5 weight percent. The inert extender then completes the formulation. Where needed, 0.1 weight percent to 1.0 weight percent of the extender may be replaced by a corrosion inhibitor or an antifoaming agent or both.

Thus, wettable powder formulations of the invention will contain from about 25 to 90 weight percent active material, from 0.5 to 2.0 weight percent wetting agent, from 0.25 to 5.0 weight percent dispersant, and from 9.25 to 74.25 weight percent inert extender, as these terms are described above.

When the wettable powder contains a corrosion inhibitor or an antifoaming agent or both, the corrosion inhibitor will not exceed about 1 percent of the composition, and the antifoaming agent will not exceed about 0.5 percent by weight of the composition, both replacing equivalent amounts of the inert extender.

B. HIGH STRENGTH COMPOSITIONS AND AQUEOUS SUSPENSION CONCENTRATES

High-strength compositions generally consist of 90 to 99.5% active ingredient and 0.5 to 10% of a liquid or solid surfactant such as those described by McCutcheon in "Detergents and Emulsifiers" 1970 Annual. Such high-strength compositions can often be used in a manner similar to the wettable powders but they are also suitable for further formulation.

The aqueous suspension concentrates are prepared by mixing together and sandgrinding an aqueous slurry of water-insoluble active ingredient in the presence of dispersing agents. Thus there is obtained a concentrated slurry of very finely divided particles in which the active ingredient is substantially all below 5 microns in size. This concentrated aqueous suspension is characterized by its extremely small particle size so that upon diluting and spraying, a very uniform coverage is obtained.

These aqueous suspension concentrates will contain from 15 to 40% of active ingredient, from 45 to 70% water with the remainder made up of surfactants, corrosion inhibitors, and suspending agents.

Suspensions in organic liquids can be prepared in a similar manner such as by replacing the water with mineral oil.

C. DUSTS

Dusts are dense powder compositions which are intended for application in dry form, in accordance with the preferred compositions and methods of the invention. Dusts are characterized by their free-flowing and rapid settling properties so that they are not readily windborne to areas where their presence is not desired. They contain primarily an active material and a dense, free-flowing, solid extender.

Their performance is sometimes aided by the inclusion of a wetting agent, and convenience in manufacture frequently demands the inclusion of an inert, absorptive grinding aid. For the dust compositions of this invention, the inert extender may be either of vegetable or mineral origin, the wetting agent is preferably anionic or nonionic, and suitable absorptive grinding aids are of mineral origin.

Suitable classes of inert solid extenders for use in the dust compositions are those organic or inorganic powders which possess high bulk density and are very free-flowing. They are also characterized by possessing relatively low surface areas and are poor in liquid absorption. Suitable classes of grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease in incorporation some liquid nonionic agents are also suitable in the dust formulations.

Preferred inert solid extenders for the dusts of this invention are micaceous talcs, pyrophyllite, dense kaolin clays, tabacco dust and ground calcium phosphate rock such as that known as "Phosphodust," a trademark of the American Agricultural Chemical Company.

Preferred grinding aids are attapulgite clay, diatomaceous silica, synthetic fine silica and synthetic calcium and magnesium silicates. preferred wetting agents are those previously described under wettable power formulations.

The inert solid extenders in the dusts of this invention are usually present in concentrations of from about 30 to 90 weight percent of the total composition. The grinding aid will usually constitute 5 to 50 weight percent of the composition, and the wetting agent will constitute from about 0 to 1.0 weight percent of the composition. Dust compositions can also contain other surfactants such as dispersing agents in concentrations of up to about 0.5 weight percent.

The wettable powders described above can also be used in the preparation of dusts. While such wettable powders could be used directly in dust form, it is more advantageous to dilute them by blending with the dense dust diluent. In this manner, dispersing agents, corrosion inhibitors, and antifoam agents may also be found as components of a dust.

Thus, the dust compositions of this invention will comprise about 5 to 20 weight percent active material, 5 to 50 weight percent absorptive filler, 0 to 1.0 weight percent wetting agent, and about 30 to 90 weight percent dense, free-flowing dust diluent, as these terms are used herein. Such dust formulations can contain, in addition, minor amounts of dispersants, corrosion inhibitors, and antifoam agents, derived from the wettable powders used to make the dusts.

D. EMULSIFIABLE OILS

Emulsifiable oils are usually solutions of active material in nonwater miscible solvents together with a surfactant.

For the compounds of this invention, emulsifiable oils can be made by mixing the active ingredient with a solvent and surfactant. Suitable solvents for the compounds of this invention are aromatic hydrocarbons including many weed oils, chlorinated solvents, and nonwater miscible ethers, esters, or ketones. Suitable surfactants are those anionic or nonionic agents known to the art as emulsifying agents. Such compounds can be found listed in "Detergents and Emulsifiers" 1970 Annual by John W. McCutcheon, Inc.

Emulsifying agents most suitable for the emulsifiable oil compositions of this invention are long-chain alkyl or mercaptan polyethoxy alcohols, alkylaryl polyethoxy alcohols, sorbitan fatty acid esters, polyoxyethylene ethers with sorbitan fatty acid esters, polyethylene glycol esters with fatty or rosin acids, fatty alkylol amide condensates, calcium and amine salts of fatty alcohol sulfates, oil soluble petroleum sulfonates or, preferably, mixtures of these emulsifying agents. Such emulsifying agents will comprise from about 1 to 10 weight percent of the total composition. As described above, however, up to 5 parts of emulsifying agent for each part of thioallophanimidate can be used.

Thus, emulsifiable oil compositions of the present invention will consist of from about 15 to 50 weight percent active material, about 40 to 82 weight percent solvent, and about 1 to 10 weight percent emulsifier, as these terms are defined and used above.

In some instances the oil solution may be intended merely for extension with other oils, such as weed oils. In this instance the emulsifying agents may be omitted and may be replaced by additional solvent.

E. GRANULES AND PELLETS

Granules and pellets are physically stable, particulate compositions containing a compound of either Formula (I) or (II) which adheres to or is distributed through a basic matrix of a coherent, inert carrier with macroscopic dimensions. In order to aid leaching of the active ingredient from the granule or pellet, a surfactant can be present.

For the compounds of this invention, the inert carrier is preferably of mineral origin, and the surfactant is a compound known in the art as a wetting agent. Such compounds are listed by J. W. McCutcheon in "Detergents and Emulsifiers" 1970 Annual.

Suitable carriers are natural clays, some pyrophyllites and vermiculite. Suitable wetting agents are anionic or nonionic.

For the granule compositions of this invention, most suitable carriers are of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15 – 30 mesh.

The most suitable wetting agents for the granular compositions of this invention depend upon the type of granule used. When preformed granules are sprayed with active material in liquid form the most suitable wetting agents are nonionic, liquid wetters miscible with the solvent. These are compounds more generally known to the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil soluble petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 weight percent active material, about 0 to 5 weight percent wetting agent, and about 65 to 95 weight percent inert material carrier, as these terms are used herein.

F. ULTRA-LOW-VOLUME APPLICATIONS

While conventional applications of sprayable formulations have usually been made in a dilute form (for example at a rate of about 220 liters/ha or more), the compounds of this invention can also be applied at higher concentrations in the typical "ultra-low-volume" or "low-volume" applications from aircraft or ground sprayers. For this purpose wettable powders can be dispersed in small amounts of aqueous or nonaqueous carrier. The suspension or emulsifiable concentrates can be used directly or with minor dilution. Special compositions particularly suitable for ULV applications are solutions or finely divided suspensions in one or more carriers such as dialkylformamides, N-alkyl pyrrolidones, dimethyl sulfoxide, water, esters, ketones, glycols, glycol ethers and the like. Other suitable carriers include aromatic hydrocarbons (halogenated and nonhalogenated), aliphatic hydrocarbons (halogenated and nonhalogenated) and the like.

The following examples provide further illustration of this invention. All percentages are give by weight unless otherwise indicated.

EXAMPLE 12

| | Percent |
|---|---|
| Methyl 4-isopropyl-N-methoxycarbonyl-1-thioallophanimidate | 40 |
| Sodium alkylnaphthalenesulfonate | 2 |
| Oleic ester of sodium isethionate | 3 |
| Attapulgite | 55 |

The above ingredients are blended and hammer milled to yield a water dispersible powder.

Forty kg of the above formulation can be suspended in 600 liters of water and applied to a bare, sandy soil around a tank farm in the spring before annual weeds emerge. The treatment will control weed growth.

EXAMPLE 13

| | Percent |
|---|---|
| Methyl 4-isopropyl-N-ethoxycarbonyl-1-thioallophanimidate | 50 |
| Dialkyl ester of sodium sulfosuccinic acid | 2 |
| Partially desulfonated sodium ligninsulfonate | 3 |
| Kaolin | 45 |

After blending, the above ingredients are micropulverized.

Ten kg of the above formulation and 2 kg of diuron [3-(3,4-dichlorophenyl)-1,1-dimethylurea] can be suspended in 400 liters of water and applied to a hectare of dormant alfalfa to control weeds.

EXAMPLE 14

| | Percent |
|---|---|
| Methyl 4-tert-butyl-N-methylthiolcarbonyl-1-thioallophanimidate | 30 |
| Calcium/magnesium ligninsulfonate | 15 |
| Hydrated attapulgite | 2 |
| Pentachlorophenol | 0.5 |
| Sodium carbonate | 2.0 |
| Water | 50.5 |

The above ingredients are mixed and then sand ground until essentially all particles of active compound are 5 microns or less.

Twenty kg of this formulation can be suspended in 400 liters of water and applied to a ratoon sugarcane field just after harvest to control numerous weeds in the cane.

Forty kg of the above formulation and three kg of bromacil (Hyvar X) can be mixed with 400 liters of water and applied as a spot treatment to areas infested with weeds. Thorough coverage of the plant foliage is essential for good postemergence control.

The following compounds may be substituted one at a time for methyl 4-tert-butyl-N-methylthiolcarbonyl-1-thioallophanimidate above in like amount by weight. When formulated and applied in like manner, like results will be obtained.

Methyl 4-isopropyl-N-ethoxycarbonyl-1-thioallophanimidate
Methyl 4-tert-butyl-N-methoxycarbonyl-1-thioallophanimidate
Methyl 4-isopropyl-N-methoxycarbonyl-1-thioallophanimidate

EXAMPLE 15

|  | Percent |
| --- | --- |
| Methyl 4-isopropyl-N-methoxycarbonyl-1-thioallophanimidate | 22 |
| Mixed polyoxyethylene ethers and oil soluble sulfonates | 10 |
| Spray oil (for example, Orchex 796) | 68 |

A mixture of the above ingredients is sand ground until essentially all particles of thioallophanimidate are 5 microns or less.

Four kg of the above formulation and one half kg of 2-chloro-4-ethylamino-6-isopropylamino-S-triazine formulated in an 80% wettable powder can be suspended in 400 liters of water and applied preemergence to corn to control weeds.

EXAMPLE 16

|  | Percent |
| --- | --- |
| Methyl 4-isopropyl-N-isopropoxycarbonyl-1-thioallophanimidate | 12 |
| Mixed polyoxyethylene ethers and oil soluble sulfonates | 10 |
| Isophorone | 78 |

Mixing the above ingredients yields a homogeneous solution which may be used directly in low volumne applications or which may be extended with water or additional solvent for conventional application.

Ten kg of the above formulation can be combined with 1 liter of paraquat and 350 liters of water and applied post-emergence to a hectare of cover crop growing where corn will be planted (silt loam soil, organic matter content 1–3%). The treatment will provide complete control of the cover crop and the corn can then be planted directly into the cover crop stubble without plowing, disking, etc. This treatment will also provide control of many serious weeds throughout the growing season of the corn.

All the active compounds of this invention may be formulated and applied in like manner.

EXAMPLE 17

|  | Percent |
| --- | --- |
| Solution of Example 14 | 20 |
| Preformed clay granules, 15–30 mesh | 80 |

The isophorone solution of active ingredient is sprayed on the preformed granules which are agitated in such a way as to obtain uniform coverage of the granules.

Fifty kg of the above granular formulation can be distributed with a spreader over a hectare of asparagus in the early spring before the spears have emerged to control weeds.

EXAMPLE 18

|  | Percent |
| --- | --- |
| Methyl 4-isopropyl-N-ethoxycarbonyl-1-thioallophanimidate | 25 |
| Anhydrous sodium sulfate | 10 |
| Calcium/magnesium ligninsulfonate | 5 |
| Sodium alkylnaphthalenesulfonate | 1 |
| Calcium/magnesium bentonite | 59 |

The above ingredients are blended, hammer milled, and then moistened with about 12% water. This mixture is extruded as approximately 3 mm diameter cylinders and cut as extruded to produce 3 mm × 3 mm pellets. These may be used as such after drying, or the dried pellets may be crushed to pass a USS No. 15 sieve. The fraction held on a USS No. 30 sieve may be packaged for use and the fines recycled.

The above pellets can be uniformly distributed along fences and pipelines at a rate of 160 kg/ha. The pellets should be applied early in the spring before vegetative growth begins. Full season control of many serious weeds will be provided thus reducing potential fire hazard and improving appearance.

The following compounds may be substituted one at a time for methyl 4-isopropyl-N-ethoxycarbonyl-1-thioallophanimidate above in like amount by weight. When formulated and applied in like manner, like results will be obtained.

Methyl 4-tert-butyl-N-methoxycarbonyl-1-thioallophanimidate
Methyl 4-tert-butyl-N-methylthiocarbonyl-1-thioallophanimidate
Methyl 4-isopropyl-N-methoxycarbonyl-1-thioallophanimidate
Methyl 4-isopropyl-N-isopropoxycarbonyl-1-thioallophanimidate

EXAMPLE 12

|  | Percent |
| --- | --- |
| Methyl 4-tert-butyl-N-methoxycarbonyl-1-thioallophanimidate | 15 |
| Polyoxyethylene ethers & esters | 4 |
| Dimethylformamide | 81 |

The above ingredients are mixed together to yield a homogeneous solution particularly suitable for low volume applications. It may, of course, also be diluted for conventional application.

Ten kg of this formulation can be mixed with 200 liters of water and applied preemergence to a hectare of corn planted in a silt loam soil containing 3% organic matter to control weeds.

All of the active compounds of this invention may be formulated and applied in like manner.

We claim:

1. A compound of the formula

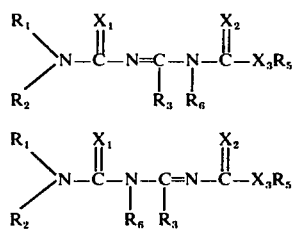

wherein
$R_1$ is hydrogen;
$R_2$ is

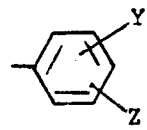

where
$Y$ is hydrogen, halogen, or methyl; and
$Z$ is halogen;
$R_3$ is $OR_4$ or $SR_4$;
$R_4$ is methyl or ethyl;
$R_5$ is methyl or ethyl;
$R_6$ is hydrogen;
$X_1$ and $X_2$ are oxygen; and
$X_3$ is oxygen or sulfur.

2. The compound of claim 1 which is methyl 4-(p-chlorophenyl)-N-methoxycarbonyl allophanimidate.

3. The compound of claim 1 which is methyl 4-(p-chlorophenyl)-N-methylthiocarbonylallophanimidate.

* * * * *